United States Patent
Foan et al.

(10) Patent No.: US 6,255,252 B1
(45) Date of Patent: Jul. 3, 2001

(54) PHENOL ESTER MIXTURE

(75) Inventors: Colin Charles Foan; Anthony Reginald Woodford, both of Brentwood (GB)

(73) Assignee: Aventis Agriculture Limited, Cambridgeshire (GB)

( * ) Notice: Subject to any disclaimer, the term of this patent is extended or adjusted under 35 U.S.C. 154(b) by 0 days.

(21) Appl. No.: 08/229,118

(22) Filed: Apr. 18, 1994

Related U.S. Application Data

(63) Continuation of application No. 08/101,787, filed on Aug. 4, 1993, now abandoned, which is a continuation of application No. 07/956,940, filed on Oct. 5, 1992, now abandoned, which is a continuation of application No. 07/846,990, filed on Feb. 12, 1992, now abandoned, which is a continuation of application No. 07/622,194, filed on Dec. 5, 1990, now abandoned, which is a continuation of application No. 07/446,382, filed on Dec. 5, 1989, now abandoned, which is a continuation of application No. 07/052,259, filed on May 20, 1987, now abandoned, which is a continuation of application No. 06/904,420, filed on Sep. 8, 1986, now abandoned, which is a continuation of application No. 06/683,560, filed on Dec. 19, 1984, now abandoned.

(30) Foreign Application Priority Data

Dec. 21, 1983 (GB) .................................................. 83 34005

(51) Int. Cl.$^7$ ...................................................... A01N 37/34
(52) U.S. Cl. ............................................................. 504/310
(58) Field of Search ............................................... 504/310

(56) References Cited

U.S. PATENT DOCUMENTS 4,332,613 * 6/1982 Esposito ................................. 71/105

FOREIGN PATENT DOCUMENTS

1067033 * 4/1967 (GB) .

* cited by examiner

*Primary Examiner*—S. Mark Clardy
(74) *Attorney, Agent, or Firm*—Burns, Doane, Swecker & Mathis, L.L.P.

(57) ABSTRACT

A mixture of the known herbicide esters 3,5-dibromo-4-hydroxybenzonitrile ("bromoxynil" n-octanoate and bromoxynil n-heptanoate is provided having a molar ratio of n-octanoate n-heptanoate from 1:1.5 to 1.5:1, which mixture possesses an unexpectedly low melting point high solubility in hydrocarbon oils. Herbicidal compositions comprising bromoxynil n-octanoate and bromoxynil n-heptanoate in such molar ratio and a method for controlling the growth of weeds with such herbicidal compositions are also provided. The ester mixture may be formed by admixture of the esters, or by reacting bromoxynil with a mixture of n-octanoic and n-heptanoic acids or of their derivatives (e.g. acid chlorides or anhydrides).

26 Claims, No Drawings

PHENOL ESTER MIXTURE

This application is a continuation, of application Ser. No. 08/101,787, filed Aug. 4. 1993, abandoned, which is a continuation of application Ser. No. 07/956,940, filed Oct. 5, 1992, abandoned, which in turn is a continuation of application Ser. No. 07/846,990, filed Feb. 12, 1992, abandoned, which in turn is a continuation of application Ser. No. 07/622,194, filed Dec. 5, 1990 (now abandoned), which in turn is a continuation of application Ser. No. 07/446,382, filed Dec. 5, 1989, abandoned which in turn is a continuation of application Ser. No. 07/052,259, filed May 20, 1987 (now abandoned), which in turn is a continuation of application Ser. No. 06/904,420, filed Sep. 8, 1986 (now abandoned), which in turn is a continuation of application Ser. No. 06/683,560, filed Dec. 19, 1984 (now abandoned).

This invention relates to a mixture of herbicidal esters of 3,5-dibromo-4-hydroxybenzonitrile and compositions containing it.

3,5-Dibromo-4-hydroxybenzonitrile (hereinafter referred to as 'bromoxynil') and bromoxynil n-octanoate, or 3,5-dibromo-4-n-octanoyloxybenzonitrile, (hereinafter referred to as 'bromoxynil octanoate') are well known herbicides which are widely used to control the growth of annual broad-leafed weeds. Bromoxynil octanoate is used extensively as a contact herbicide for the control of seedlings of broad-leafed weeds in cereal crops and to control perennial weeds in industrial and other non-crop situations.

Bromoxynil octanoate is a cream-coloured waxy solid, which when pure, melts at 45–46° C. The grade of bromoxynil octanoate used commercially as a herbicide is usually somewhat less pure and melts at 40–44° C. Bromoxynil octanoate is practically insoluble in water at 25° C. and, for use as a herbicide, it is usually formulated as a liquid concentrate comprising a solution in a suitable hydrocarbon oil, together with conventional additives, e.g. emulsifying agents, which concentrate is diluted with water to give spray fluids suitable for application to weeds. Commercially available liquid concentrates contain up to 240 g per liter of bromoxynil phenol equivalent. (By the term 'phenol equivalent' is meant the 3,5-dibromo-4-hydroxybenzonitrile moiety content of the formulation).

The n-heptanoic ester of bromoxynil, 3,5-dibromo-4-n-heptanoyloxybenzonitrile (hereinafter referred to as 'bromoxynil heptanoate'), a cream-coloured waxy solid melting at 39.0° C., possesses herbicidal properties similar to those of bromoxynil octanoate and may be formulated and used in a similar fashion, but bromoxynil heptanoate has not hitherto been widely used as a herbicide. Bromoxynil octanoate and bromoxynil heptanoate may be prepared by known processes, for example as described in British Patent Specification No 1067033, by the esterification of 3,5-dibromo-4-hydroxybenzonitrile with n-octanoic acid anhydride and n-heptanoic acid anhydride, respectively.

As a waxy solid at normal ambient temperature, bromoxynil octanoate is less convenient to handle and transport than would be the case if it were a liquid at the same temperature. Furthermore, when preparing herbicidal liquid concentrates, it is necessary to melt the bromoxynil octanoate in order to facilitate mixing with the hydrocarbon oil and, if desired, conventional additives. This need to melt the bromoxynil octanoate necessitates the use of valuable energy which would otherwise be avoided.

As a result of research and experimentation, it has been found that a substantially 1:1 molar ratio mixture of bromoxynil octanoate and bromoxynil heptanoate, i.e. a mixture comprising substantially 50 molar percent of bromoxynil octanoate and substantially 50 molar percent of bromoxynil heptanoate, possesses an unexpectedly lower melting point than bromoxynil octanoate alone or bromoxynil heptanoate alone, or mixtures thereof in other proportions, which lower melting point renders the aforesaid substantially 1:1 molar ratio mixture of bromoxynil octanoate and bromoxynil heptanoate particularly advantageous in terms of ease of transportation, handling and formulation into herbicidal liquid concentrates and in the reduction of energy input necessary in the preparation of herbicidal liquid concentrates.

The aforesaid substantially 1:1 ratio molar mixture of bromoxynil octanoate and bromoxynil heptanoate possesses herbicidal properties very similar to those of bromoxynil octanoate and formulations of the mixture may be used in the same manner and at the same rates of application as bromoxynil octanoate to control the growth of weeds.

The substantially 1:1 molar ratio mixture of bromoxynil octanoate and bromoxynil heptanoate according to the present invention may be prepared by mixing the appropriate amounts of bromoxynil octanoate and bromoxynil heptanoate or by reacting bromoxynil with a substantially 1:1 molar ratio mixture of suitable reactive derivatives of n-octanoic acid and n-heptanoic acid, for example a substantially 1:1 molar ratio mixture of n-octanoic acid anhydride and n-heptanoic acid anhydride or a substantially 1:1 molar ratio mixture of n-octanoyl chloride and n-heptanoyl chloride.

By the term 'substantially 1:1 molar ratio mixture' as used in the present specification in respect of mixtures of bromoxynil octanoate and bromoxynil heptanoate and mixtures of suitable reactive derivatives of n-octanoic acid and n-heptanoic acid, is meant mixtures wherein the molar ratio of bromoxynil octanoate to bromoxynil heptanoate and reactive derivative of n-octanoic acid to reactive derivative of n-heptanoic acid, is from 1:1.5 to 1.5:1, preferably 1:1.02 to 1.02:1, and more especially 1:1.

The unexpectedly low melting point of the substantially 1:1 molar ratio mixture of bromoxynil octanoate and bromoxynil heptanoate in comparison with bromoxynil octanoate alone or bromoxynil heptanoate alone or mixtures thereof in other proportions has been demonstrated in the following experiment:

Experiment 1

Mixtures of bromoxynil octanoate and bromoxynil heptanoate in the molar ratios indicated in the following Table I were prepared by mixing appropriate amounts of the two esters. Each mixture was then melted and the molten mass was stirred to render it homogenous. The molten mass was then rapidly cooled to −10° C. by external cooling. A sample of the crystals from the solid frozen mass thus obtained was placed in a capillary tube which was then placed in a stirred water bath. The temperature of the water bath was raised at a rate of 0.5° C. per minute and the temperature at which a meniscus first appeared in the tube was recorded as the melting point of the mixture in question.

The results obtained are given in the following Table I.

TABLE I

| Molar percentage of Bromoxynil octanoate in mixture | Molar percentage of Bromoxynil heptanoate in mixture | Melting point (° C.) |
|---|---|---|
| 100 | 0 | 44.5 |
| 88.1 | 11.9 | 41.5 |
| 78.1 | 21.9 | 38.5 |
| 69.7 | 30.3 | 35.0 |
| 57.4 | 42.6 | 30.0 |
| 48.8 | 51.2 | 22.0 |
| 38.1 | 61.9 | 28.0 |
| 26.9 | 73.1 | 33.0 |
| 17.7 | 82.3 | 34.0 |
| 9.4 | 90.6 | 37.0 |
| 0 | 100 | 39.0 |

As already mentioned, bromoxynil octanoate is commercially available as a liquid concentrate comprising a solution of up to 240 g per liter of bromoxynil phenol equivalent in a suitable hydrocarbon oil, together with conventional additives, e.g. emulsifying agents. For reasons of convenience and economy, liquid concentrates containing the maximum amount of bromoxynil octanoate are preferred. Such liquid concentrates are frequently distributed and marketed during the winter months involving transportation and storage at relatively low temperature. With commercially available formulations comprising 240 g per liter of bromoxynil octanoate in a suitable hydrocarbon oil, crystallisation may begin to occur at temperatures as high as −7° C. The occurrence of crystallisation in such bromoxynil octanoate liquid formulations presents a serious problem since the formulations are thereby rendered less effective or even completely unusable and the crystals are, in practice, extremely difficult to re-dissolve. It is, therefore, usually necessary to take special precautions in transport and storage to avoid permitting the temperature of the liquid formulations to fall to a level at which crystallisation occurs.

The substantially 1:1 molar ratio mixture of bromoxynil octanoate and bromoxynil heptanoate provided according to the present invention provides the further unexpected advantage of possessing significantly greater solubility in hydrocarbon oils than bromoxynil octanoate alone, bromoxynil heptanoate alone or mixtures of bromoxynil octanoate and bromoxynil heptanoate in other molar ratios, thereby permitting liquid formulations to be prepared comprising a solution of a substantially 1:1 molar ratio mixture of bromoxynil octanoate and bromoxynil heptanoate in a suitable hydrocarbon oil, e.g. mineral oils and more especially mineral oils having a flash point higher than 34° C. Suitable mineral oils include, in particular, mineral oils having a high aromatic content, preferably of at least 80% and a flash point higher than 37° C., and more especially light aromatic mineral oils containing about 85% $C_9$- or $C_{10}$-alkylbenzenes of b.p. 165 to 210° C., but suitable mineral oils also include essentially aliphatic mineral oils, for example aliphatic mineral oils with an aromatic content of about 15% volume/volume and a flash point higher than 34° C., containing a given amount of bromoxynil phenol equivalent which crystallizes at a significantly lower temperature than a solution of bromoxynil octanoate alone, bromoxynil heptanoate alone or mixtures of bromoxynil octanoate and bromoxynil heptanoate in other molar ratios in the same hydrocarbon oil containing the same given amount of bromoxynil phenol equivalent or permitting liquid formulations to be prepared comprising a solution of a substantially 1:1 molar ratio mixture of bromoxynil octanoate and bromoxynil heptanoate in a suitable hydrocarbon oil containing a substantially greater concentration of bromoxynil phenol equivalent than solutions of bromoxynil octanoate alone, bromoxynil heptanoate alone or mixtures of bromoxynil octanoate and bromoxynil heptanoate in other molar ratios in the same suitable hydrocarbon oil which crystallize at the same temperature.

The significantly lower temperature at which crystallisation of a solution of a substantially 1:1 molar ratio mixture of bromoxynil octanoate and bromoxynil heptanoate in a hydrocarbon oil occurs, in comparison with similar solutions of bromoxynil octanoate alone, bromoxynil heptanoate alone and mixtures of bromoxynil octanoate and bromoxynil heptanoate in other molar ratios, has been demostrated in the following experiments:

Experiment 2

A solution of bromoxynil octanoate was prepared by dissolving 71.2 g of bromoxynil octanoate (containing 92% of bromoxynil octanoate) in 100 ml of Solvesso 150. A solution of bromoxynil heptanoate was prepared by dissolving 66.3g of bromoxynil heptanoate (containing 93.8% bromoxynil heptanoate) in 100 ml of Solvesso 150 (Solvesso 150 is a light aromatic mineral oil containing about 85% $C_{10}$ alkylbenzenes, b.p. 190–210° C.; flash point 62 to 63° C.).

Portions of these solutions of bromoxynil octanoate and bromoxynil heptanoate in the following proportions were then placed and mixed thoroughly in glass tubes.

| Solution | Bromoxynil octanoate solution (ml) | Bromoxynil heptanoate solution (ml) |
|---|---|---|
| A | 10 | 0 |
| B | 9 | 1 |
| C | 8 | 2 |
| D | 7 | 3 |
| E | 6 | 4 |
| F | 5 | 5 |
| G | 4 | 6 |
| H | 3 | 7 |
| I | 2 | 8 |
| J | 1 | 9 |
| K | 0 | 10 |

The tubes were cooled to −20° C. and then heated under visual examination in such a manner that the temperature rose at a rate of 0.25° C. per minute, with gentle stirring of each tube. The temperature at which crystalline material in the tube disappeared was recorded as the re-solution temperature.

The results obtained are given in the following Table II.

TABLE II

| Solution | Molar ratio Bromoxynil octanoate:Bromoxynil heptanoate | Re-solution temperature (° C.) |
|---|---|---|
| A | 100:0 | 41 |
| B | 90.1:9.9 | 39 |
| C | 80.3:19.7 | 30 |
| D | 70.3:29.7 | 21 |
| E | 60.4:39.6 | 15 |
| F | 50.4:49.6 | 4 |

TABLE II-continued

| Solution | Molar ratio Bromoxynil octanoate:Bromoxynil heptanoate | Re-solution temperature (° C.) |
|---|---|---|
| G | 40.4:59.6 | 10 |
| H | 30.3:69.7 | 26 |
| I | 20.3:79.7 | 29 |
| J | 10.1:89.9 | 31 |
| K | 0:100 | 32 |

Experiment 3

Ten gram quantities of bromoxynil octanoate alone, bromoxynil heptanoate alone and mixtures of bromoxynil octanoate and bromoxynil heptanoate in varying proportions by weight were placed in glass tubes, the samples in each tube being as indicated below in Table III.

TABLE III

| Sample | Bromoxynil octanoate (g) | Bromoxynil heptanoate (g) |
|---|---|---|
| A | 10 | 0 |
| B | 6.15 | 3.85 |
| C | 5.83 | 4.17 |
| D | 5.45 | 4.55 |
| E | 5 | 5 |
| F | 4.55 | 5.45 |
| G | 4.17 | 5.83 |
| H | 3.85 | 6.15 |
| I | 0 | 10 |

Carless Standard White Spirit (Carless Standard White Spirit is a light aliphate mineral oil containing 15% volume/volume of aromatic hydrocarbons, bp 150–200° C., flash point 35° C.) was added to each tube to a final volume of 10 ml, to give corresponding solutions A to I. The tubes were cooled to 0° C. and then heated under visual examination in such a manner that the temperature rose at a rate of 0.25° C. per minute, with gentle stirring of each tube. The temperature at which crystalline material in a tube disappeared was recorded as the re-solution temperature. The results obtained are given in the following Table IV.

TABLE IV

| Solution | Molar ratio Bromoxynil octanoate:Bromoxynil heptanoate | Re-solution temperature (° C.) |
|---|---|---|
| A | 100:0 | 29 |
| B | 61.3:38.7 | 24 |
| C | 58.1:41.9 | 23.5 |
| D | 54.3:45.7 | 22 |
| E | 49.8:50.2 | 18 |
| F | 45.4:54.6 | 21 |
| G | 41.6:58.4 | 22 |
| H | 38.4:61.6 | 22.5 |
| I | 0:100.0 | 28 |

Experiment 4

Ten gram quantities of bromoxynil octanoate alone, bromoxynil heptanoate alone and mixtures of bromoxynil octanoate and bromoxynil heptanoate in varying proportions by weight were placed In glass tubes, the samples in each tube being as indicated below in Table V.

TABLE V

| Sample | Bromoxynil octanoate (g) | Bromoxynil heptanoate (g) |
|---|---|---|
| A | 10 | 0 |
| B | 6.15 | 3.85 |
| C | 5.83 | 4.17 |
| D | 5.45 | 4.55 |
| E | 5 | 5 |
| F | 4.55 | 5.45 |
| G | 4.17 | 5.83 |
| H | 3.85 | 6.15 |
| I | 0 | 10 |

Shellsol A (Shellsol A is a light aromatic mineral oil containing 98% volume/volume of aromatic hydrocarbons approximate composition 1:2:4 trimethyl benzene 31% w/w; other $C_9$ aromatics 48% w/w; $C_{10}$ aromatics 18% w/w; $C_8$ aromatics 1% w/w; bp 166–185° C.; flash point 43° C.) was added to each tube to a final volume of 10 ml, to give corresponding Solutions A to I. The tubes were cooled to –15° C. and then heated under visual examination in such a manner that the temperature rose at a rate of 0.25° C. per minute, with gentle stirring of each tube. The temperature at which crystalline material in a tube disappeared was recorded as the re-solution temperature. The results obtained are given in the following Table VI.

TABLE VI

| Solution | Molar ratio Bromoxynil octanoate:Bromoxynil heptanoate | Re-solution temperature (° C.) |
|---|---|---|
| A | 100:0 | 34 |
| B | 61.3:38.7 | 22 |
| C | 58.1:41.9 | 16 |
| D | 54.3:45.7 | 11 |
| E | 49.8:50.2 | 2 |
| F | 45.4:54.6 | 11 |
| G | 41.6:58.4 | 17 |
| H | 38.4:61.6 | 23 |
| I | 0:100.0 | 36 |

Accordingly, there are provided, as a further feature of the present invention, solutions of a substantially 1:1 molar ratio mixture of bromoxynil octanoate and bromoxynil heptanoate in suitable hydrocarbon oils, e.g. mineral oils having a high aromatic content and more especially mineral oils having a flash point higher than 37° C. and an aromatic content of at least 80%, and in particular a light aromatic mineral oil containing about 85% $C_{10}$ alkylbenzenes, bp 190–210° C., which preferably contain from 1 g per liter to 500 g per liter of bromoxynil phenol equivalent.

According to a further feature of the present invention there are provided liquid herbicide concentrates suitable for dilution with water to give spray fluids suitable for application to weeds, which comprise solutions of a substantially 1:1 molar ratio mixture of bromoxynil octanoate and bromoxynil heptanoate and suitable emulsifying agents, which may be of the ionic or non-ionic types, for example sulphoricinoleates, quaternary ammonium derivatives, products based on condensates of ethylene oxide with alkyl, e.g. nonyl or octyl, or polyaryl phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphono-succinates, alkali and alkaline earth metal salts of high molecular weight sulphonic acid derivatives such as sodium and calcium lignosulphonates and sodium and calcium alkyl benzene sulphonates, preferably in an amount of from 0.1% to 12.0% weight/volume, in suitable hydrocarbon oils, e.g. mineral oils and more especially mineral oils having a flash point higher than 34° C. Suitable mineral oils include, in particular, mineral oils having a high aromatic content, preferably of at least 80%, and a flash point higher than 37° C., and more especially light aromatic mineral oils containing about 85% $C_9$- or $C_{10}$-alkylbenzenes of b.p. 165 to 210° C., but suitable mineral oils also include essentially aliphatic mineral oils, for example aliphatic mineral oils with an aromatic content of about 15% volume/volume and a flash point higher than 34° C. Preferably, liquid herbicidal compositions according to the present invention comprise from 1 g per liter to 500 g per liter of bromoxynil phenol equivalent. Liquid herbicide concentrates according to the present invention may also, if desired, comprise other herbicides which possess adequate solubility in the hydrocarbon oil to form a solution, e.g. phenoxyalkanoic acid esters, and in particular esters, e.g. iso-octylesters, of (2,4-dichlorophenoxy)acetic acid, (4-chloro-2-methyl-phenoxy)acetic acid or (±)-2-(4-chloro-2-methyl-phenoxy)propionic acid. The amounts of other herbicides which may be included in liquid herbicide concentrates according to the present invention depend upon the solubility of the aforesaid other herbicides and the herbicidal effect which is desired.

Spray fluids suitable for application to weeds to control their growth obtained by the dilution with water of liquid herbicide concentrates according to the present invention and a method for controlling the growth of weeds, more especially annual broad-leafed weeds, which comprises applying such spray fluids to the weeds, form further features of the present invention. Spray fluids suitably contain from 0.015% to 2.0% weight/volume of a substantially 1:1 molar ratio mixture of bromoxynil octanoate and bromoxynil heptanoate and are applied to control the growth of broad-leafed weeds at application rates of from 100 g to 1.0 kg per hectare of bromoxynil phenol equivalent.

The following Examples illustrate the present invention:

EXAMPLE 1

A solution suitable for use as a herbicidal concentrate containing 450 g per liter of bromoxynil phenol equivalent was prepared by dissolving bromoxynil octanoate and bromoxynil heptanoate in Solvesso 150 light aromatic mineral oil in proportions such that the molar ratio of bromoxynil octanoate to bromoxynil heptanoate was 50.4:49.6. A mixture of emulsifying agents [1:1 mixture of Arylan CA (70% solution calcium dodecyl benzene sulphonate in butanol) and Ethylan BCP (nonyl phenol nine mole ethoxylate)] was then added in an amount of 100 g per liter. The solution thus obtained was found not to crystallize at temperatures down to −7° C.

EXAMPLE 2

A solution suitable for use as a herbicidal concentrate containing 375 g per liter of bromoxynil phenol equivalent was prepared by dissolving bromoxynil octanoate and bromoxynil heptanoate in Shellsol A light aromatic mineral oil in proportions such that the molar ratio of bromoxynil octanoate to bromoxynil heptanoate was 50.4:49.6. A mixture of emulsifying agents [1:1 mixture of Arylan CA (70% solution calcium dodecyl benzene sulphonate in butanol) and Ethylan BCP (nonyl phenol nine mole ethoxylate)] was then added in an amount of 80 g per liter. The solution thus obtained was found not to crystallize at temperatures down to −10° C.

EXAMPLE 3

A solution suitable for use as a herbicidal concentrate containing 250 g per liter of bromoxynil phenol equivalent was prepared by dissolving bromoxynil octanoate and bromoxynil heptanoate in Carless Standard White Spirit in proportions such that the molar ratio of bromoxynil octanoate to bromoxynil heptanoate was 50.4:49.6. A mixture of emulsifying agents [1:1 mixture of Arylan CA (70% solution calcium dodecyl benzene sulphonate in butanol) and Ethylan BCP (nonyl phenol nine mole ethoxylate)] was then added in an amount of 80 g per liter. The solution thus obtained was found not to crystallize at temperatures down to −7° C.

What is claimed is:

1. A mixture of bromoxynil n-octanoate and bromoxynil n-heptanoate wherein the molar ratio of bromoxynil n-octanoate to bromoxynil n-heptanoate is from 1:1.5 to 1.5:1.

2. A mixture according to claim 1 wherein the molar ratio of bromoxynil n-octanoate to bromoxynil n-heptanoate is from 1:1.02 to 1.02:1.

3. A mixture according to claim 1 wherein the molar ratio of bromoxynil n-octanoate to bromoxynil n-heptanoate is 1:1.

4. A process for preparing a mixture of bromoxynil n-octanoate and bromoxynil n-heptanoate wherein the molar ratio of bromoxynil n-octanoate to bromoxynil n-heptanoate is from 1:1.5 to 1.5:1 which comprises mixing bromoxynil n-octanoate and bromoxynil n-heptanoate in the molar ratio of bromoxynil n-octanoate to bromoxynil n-heptanoate of 1:1.5 to 1.5:1.

5. A solution of bromoxynil n-octanoate and bromoxynil n-heptanoate in a suitable hydrocarbon oil wherein the molar ratio of bromoxynil n-octanoate to bromoxynil n-heptanoate is from 1:1.5 to 1.5:1.

6. A solution according to claim 5 wherein the molar ratio of bromoxynil n-octanoate to bromoxynil n-heptanoate is from 1:1.02 to 1.02:1.

7. A solution according to claim 5 wherein the molar ratio of bromoxynil n-octanoate to bromoxynil n-heptanoate is 1:1.

8. A solution according to claim 5 wherein the suitable hydrocarbon oil is a mineral oil.

9. A solution according to claim 5 wherein the suitable hydrocarbon oil is a mineral oil having a flash point higher than 34° C.

10. A solution according to claim 5 wherein the suitable hydrocarbon oil is a mineral oil having a high aromatic content.

11. A solution according to claim 5 wherein the suitable hydrocarbon oil is a mineral oil having a flash point higher than 37° C. and an aromatic content of at least 80%.

12. A solution according to claim 5 wherein the suitable hydrocarbon oil is a light aromatic mineral oil containing about 85 % $C_9$ or $C_{10}$alkyl-benzenes, b.p. 165–210° C.

13. A solution according to claim 5 wherein the suitable hydrocarbon oil is an aliphatic mineral oil.

14. A solution according to claim 5 wherein the suitable hydrocarbon oil is an aliphatic mineral oil with an aromatic content of 15% volume/volume, bp 150–200° C.

15. A solution according to claim 5 which contains from 1 g per liter to 500 g per liter of 3,5-dibromo-4-n-heptanoyloxybenzonitrile moiety of the bromoxynil n-octanoate and bromoxynil n-heptanoate.

16. A liquid herbicide concentrate suitable for dilution with water to give spray fluids suitable for application to weeds to control their growth, which comprises a solution of a mixture of bromoxynil n-octanoate and bromoxynil n-heptanoate wherein the molar ratio of bromoxynil n-octanoate to bromoxynil n-heptanoate is from 1:1.5 to 1.5:1, and suitable emulsifying agents in a suitable hydrocarbon oil.

17. A liquid herbicide concentrate according to claim 16 wherein the molar ratio of bromoxynil n-octanoate to bromoxynil n-heptanoate is from 1:1.02 to 1.02:1.

18. A liquid herbicide concentrate according to claim 16 wherein the molar ratio of bromoxynil n-octanoate to bromoxynil n-heptanoate is 1:1.

19. A liquid herbicide concentrate according to claim 18, which comprises from 0.1% to 12.0% weight/volume of emulsifying agent.

20. A liquid herbicide concentrate according to claim 16 wherein the suitable hydrocarbon oil is a mineral oil as defined in anyone of claims 11 to 16.

21. A liquid herbicide concentrate according to claim 16 which contains from 1 g per liter to 500 g per liter of bromoxynil phenol equivalent.

22. A spray fluid suitable for application to weeds to control their growth obtained by the dilution with water of a liquid herbicide composition according to claim 16.

23. A spray fluid according to claim 22 which comprises from 0.015% to 2.0% weight/volume of a mixture of bromoxynil n-octanoate and bromoxynil n-heptanoate wherein the molar ratio of bromoxynil n-octanoate to bromoxynil n-heptanoate is from 1:1.5 to 1.5:1.

24. A spray fluid according to claim 22 which comprises from 0.015% to 2.0% weight/volume of a mixture of bromoxynil n-octanoate and bromoxynil n-heptanoate wherein the molar ratio of bromoxynil n-octanoate to bromoxynil n-heptanoate is from 1:1.02 to 1.02:1.

25. A spray fluid according to claim 22 which comprises from 0.015% to 2.0% weight/volume of a mixture of bromoxynil n-octanoate and bromoxynil n-heptanoate wherein the molar ratio of bromoxynil n-octanoate to bromoxynil n-heptanoate is 1:1.

26. A method for the control of the growth of weeds which comprises the application to the weeds of a spray fluid according to claim 22 in an amount sufficient to provide an application rate of from 100 g to 1.0 kg per hectare of 3,5-dibromo-4-n-heptanoyloxybenzonitrile moiety of the bromoxynil n-octanoate and bromoxynil n-heptanoate.

* * * * *